US012590093B2

(12) United States Patent
Si et al.

(10) Patent No.: US 12,590,093 B2
(45) Date of Patent: Mar. 31, 2026

(54) INDOLO[2',3':3,4]PYRIDO[2,1-B]QUINAZOLINE COMPOUND AND USE THEREOF

(71) Applicant: INSTITUTE OF MEDICINAL BIOTECHNOLOGY CHINESE ACADEMY OF MEDICAL SCIENCES, Beijing (CN)

(72) Inventors: Shuyi Si, Beijing (CN); Yanni Xu, Beijing (CN); Xiao Wang, Beijing (CN); Jinque Luo, Beijing (CN); Yongzhen Li, Beijing (CN); Chao Liu, Beijing (CN); Xinhai Jiang, Beijing (CN); Yining Li, Beijing (CN); Xiaowan Han, Beijing (CN); Yan Li, Beijing (CN); Minghua Chen, Beijing (CN); Jing Zhang, Beijing (CN); Xin Zhen, Beijing (CN)

(73) Assignee: INSTITUTE OF MEDICINAL BIOTECHNOLOGY CHINESE ACADEMY OF MEDICAL SCIENCES, Beijing (CN)

( * ) Notice: Subject to any disclaimer, the term of this patent is extended or adjusted under 35 U.S.C. 154(b) by 984 days.

(21) Appl. No.: 17/767,218

(22) PCT Filed: Sep. 27, 2020

(86) PCT No.: PCT/CN2020/118068

§ 371 (c)(1),
(2) Date: Apr. 7, 2022

(87) PCT Pub. No.: WO2021/068773

PCT Pub. Date: Apr. 15, 2021

(65) Prior Publication Data

US 2022/0402918 A1 Dec. 22, 2022

(30) Foreign Application Priority Data

Oct. 8, 2019 (CN) ........................ 201910948669.6

(51) Int. Cl.

| | |
|---|---|
| ***C07D 471/14*** | (2006.01) |
| ***A61P 3/06*** | (2006.01) |
| ***A61P 9/10*** | (2006.01) |
| ***A61P 29/00*** | (2006.01) |
| ***C07D 471/22*** | (2006.01) |
| ***C07D 498/14*** | (2006.01) |

(52) U.S. Cl.

CPC .............. *C07D 471/14* (2013.01); *A61P 3/06* (2018.01); *A61P 9/10* (2018.01); *A61P 29/00* (2018.01); *C07D 471/22* (2013.01); *C07D 498/14* (2013.01)

(58) Field of Classification Search

CPC .. C07D 471/14; C07D 471/22; C07D 498/14; A61P 9/10; A61P 3/06; A61P 29/00

USPC ........................................................ 514/229.5

See application file for complete search history.

(56) References Cited

FOREIGN PATENT DOCUMENTS

| | | | |
|---|---|---|---|
| CN | 102311434 | B | 8/2013 |
| CN | 103992336 | B | 1/2017 |
| WO | WO-2012126280 | A1 | 9/2012 |
| WO | WO-2018188446 | A1 | 10/2018 |

OTHER PUBLICATIONS

Luo et al., Rutaecarpine derivative R3 attenuates atherosclerosis via inhibiting NLRP3 inflammasome-related inflammation and modulating cholesterol transport, 2020, The FASEB Journal, 34, 1398-1411 (Year: 2020).*

Chen et al., Synthesis and vasodilator effects of rutaecarpine analogues which might be involved transient receptor potential vanilloid subfamily, member 1 (TRPV1), 2009, Bioorganic & Medicinal Chemistry, 17, 2351-2359 (Year: 2009).*

Wansi et al., Bioactive beta-indoloquinazoline Alkaloids from Oricia renieri, 2012, Planta Med, 78, 71-75 (Year: 2012).*

Xu, Y., et al., "Rutaecarpine suppresses atherosclerosis in ApoE $^{-/-}$ mice through upregulating ABCA1 and SR-BI within RCT," Journal of Lipid Research, 55: 1634-1647 (2014).

Wan, X., et al., "5'-AMP-Activated Protein Kinase-Activating Transcription Factor 1 Cascade Modulates Human Monocyte-Derived Macrophages to Atheroprotective Functions in Response to Heme or Metformin," Arterioscler Thromb Vasc Biol, 33: 2470-2480 (2013).

Majdalawieh, A., and Ro, H.S., PPARγ1 and LXRα face a new regulator of macrophage cholesterol homeostasis and inflammatory responsiveness, AEBP, NRS, 8: 1-17 (2010).

(Continued)

*Primary Examiner* — Kristin A Vajda

(74) *Attorney, Agent, or Firm* — Harness Dickey & Pierce P.L.C.

(57) ABSTRACT

The disclosure relates to an indolo[2',3':3,4]pyrido[2,1-b]quinazoline compound represented by general formula (I) and use thereof in the manufacture of (1) a medicament for treating a cardiovascular and cerebrovascular disease, (2) a formulation for increasing expression of AMPK, ABCA1 and SR-BI, (3) a formulation for activating nuclear receptors (NRs), and inhibiting activity of NLRP3, IL-1β, NF-κB and MAPKs, (4) a formulation for promoting cellular cholesterol efflux; or (5) a medicament for anti-inflammation.

(I)

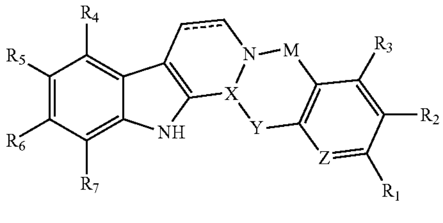

4 Claims, 6 Drawing Sheets

(56) References Cited

OTHER PUBLICATIONS

Zeller, I., and Srivastava, S., "Macrophage Functions in Atheroschlerosis," Circ Res., 115: e83-e85 (2014).
De Jager, S.C.A., and Pasterkamp, G., "Crosstalk of lipids and inflammation in atherosclerosis: the PRO of PGRN?" Cardiovascular Research, 100: 4-6 (2013).
Quintans, J.S.S., et al., "Monoterpenes modulating cytokines—a review," Food and Chemical Toxicology, p. 1-94 (2018).
Qiao, Y., et al., "TLR-induced NF-κB activation regulates NLRP3 expression in murine macrophages," FEBS Letters: 586: 1022-1026 (2012).
Ridker, P.M., et al., "Relationship of C-reactive protein reduction to cardiovascular event reduction following treatment with canakinumab: a secondary analysis from the CANTOS randomised controlled trial," Articles, p. 1-10 (2017).
Duewell, P., et al., "NLRP3 inflammasomes are required for atherogenesis and activated by cholesterol crystals," Nature, 466 (2010).
Olofsson, P.S., et al., "A Functional Interleukin-1 Receptor Antagonist Polymorphism Influences Atherosclerosis Development," Circ J., 73: 1531-1536 (2009).
Guo, H., et al., "Inflammasomes: mechanism of action, role in disease, and therapeutics," Nature Medicine, 21(7): 677-687 (2015).
Xu, S., et al., "Targeting epigenetics and non-coding RNAs in atherosclerosis: from mechanisms to therapeutics," Pharmacology & Therapeutics, 196: 15-43 (2019).
Libby, P., "Inflammation in atherosclerosis," Nature, 420: 868-874 (2002).
Wang, Z., et al., "One-Pot Total Synthesis of Evodiamine and Its Analogues through a Continuous Biscyclization Reaction," Org. Lett., 20: 6380-6383 (2018).
Granger, B.A., et al., "Multicomponent Assembly Processes for the Synthesis of Diverse Yohimbine and Corynanthe Alkaloid Analogues," ACS Comb. Sci., 15: 379-386 (2013).
Martins, G.R., et al., "Structure-Activity Relationship Study of Rutaecarpine Analogous Active Against Central Nervous System Cancer," J. Braz. Chem. Soc., 23(12): 2183-2190 (2012).
Wang, R., et al., "Monolithic column with polymeric deep eutectic solvent as stationary phase for capillary electrochromatography," Journal of Chromatography, 1577: 1-6 (2018).
Kim, S.I., et al., "New Topoisomerases Inhibitors: Synthesis of Rutaecarpine Derivatives and Their Inhibitory Activity against Topoisomerases," Arch Pharm Res, 35(5): 785-789 (2012).
Pachter, I.J., et al., "The Chemistry of Hortiamine and 6-Methoxyrthetsinine," Journal of the American Chemistry Society, 83: 635-642 (1961).
Deng, J., et al., "A concise synthesis and biological study of evodiamine and its analogues," Chem. Commun. 55: 3089-3092 (2019).
Richers, M.T., et al., "Redox-Neutral α-Oxygenation of Amines: Reaction Development and Elucidation of the Mechanism," JACS, 136(16): 6123-6135 (2014).
Bergman, J., and Bergman, S., "Studies of Rutaecarpine and Related Quinazolinocarboline Alkaloids," Journal of Organic Chemistry, 50(8): 1246-1255 (1985).
Sainsbury, M., and Uttley, N.L., "Chemical and Photochemical Cyclisations of 1-Alkylidene-1,2,3,4-tetra-hydro-2-nicotinoyl- and - isonicotinoyl-β-carbolines: A Regiospecific Synthesis of Nauclefine," Journal of the Chemical Society, 19: 2109-2115 (1977).
Knolker, H., and Cammerer, S., "Transition metal complexes in organic synthesis. part 62:[1] Total synthesis of (±)-demethoxycarbonyldihydrogambirtannine and norketoyobyrine by an iron-mediated [2+2+1] cycloaddition," Tetrahedron Letters, 41: 5035-5038 (2000).
Petrocellis, L.D., et al., "Effect of chirality and lipophilicity in the functional activity of evodiamine and its analogues at TRPV1 channels," British Journal of Pharmacology, 171(10): 1-36 (2013).
Dong, G., et al., "New Tricks for an Old Natural Product: Discovery of Highly Potent Evodiamine Derivatives as Novel Antitumor Agents by Systemic Structure—Activity Relationship Analysis and Biological Evaluations," Journal of Medicinal Chemistry, 55(17): 1-21 (2012).
Sanchez-Sancho, F., et al., "Efficient Syntheses of Polyannular Heterocycles Featuring Microwave—Accelerated Bischler—Napieralski Reaction, Stereoselective Heck Cyclization, and Claisen Rearrangement," Letter, 4: 509-513 (2000).
Wang, C., et al., "Rutaecarpine alleviates renal ischemia reperfusion injury in rats by suppressing the JNK/p38 MAPK signaling pathway and interfering with the oxidative stress response," Molecular Medicine Reports, 16: 922-928 (2017).
Database Registry, compound 851067-39-5 (2014).
Database Registry, compound 788799-56-4 (2014).
Database Registry, compound 775556-69-9 (2014).
Database Registry, compound 758662-99-6 (2014).
Database Registry, compound 756795-67-2 (2014).
Database Registry, compound 740779-51-5 (2014).
Database Registry, compound 150339-31-4 (2014).
Database Registry, compound 1355078-04-4 (2014).
International Search Report from corresponding PCT Application No. PCT/CN2020/118068 dated Dec. 31, 2020.
Office Action from corresponding Chinese Application No. 201910948669.6 dated Jun. 17, 2020.

* cited by examiner

A
TR2
TR3
TR4

T-C1
TR6
B

C

TY4 R = H
TY3
D

INDOLO[2',3':3,4]PYRIDO[2,1-B]QUINAZOLINE COMPOUND AND USE THEREOF

CROSS-REFERENCE TO RELATED APPLICATIONS

This patent application is national stage application under 35 U.S.C. § 371 of International Application No. PCT/CN2020/118068 filed on 27 Sep. 2020, which claims priority to Chinese Application No. 201910948669.6 filed on 8 Oct. 2019. The entire disclosures of each of the above recited applications are incorporated herein by reference.

FIELD OF THE INVENTION

The present disclosure belongs to the field of medicinal biotechnology, and in particular, relates to an indolo[2',3':3,4]pyrido[2,1-b]quinazoline compound and use thereof.

BACKGROUND OF THE INVENTION

Atherosclerosis is a chronic disease characterized by lipid deposition and inflammatory response. The inflammation of the blood vessel wall is a key factor in the initiation and development of atherosclerosis (Libby, P., et al., Inflammation in atherosclerosis. Nature, 2002. 420: 868-874.) The modification and deposition of lipids in plaque is one major function of the inflammatory mediators in atherosclerosis (Xu, S., et al., Targeting epigenetics and non-coding RNAs in atherosclerosis: from mechanisms to therapeutics. Pharmacology & therapeutics, 2019. 196: 15-43.). Early anti-atherosclerotic drugs are mainly characterized by lipid-lowering, of which statins are typical representatives. Although statins can effectively lower cholesterol level, the effective intervention rate of statins on cardiovascular events is only 30%-40%. In addition, statins have side effects including severe liver and kidney toxicity and rhabdomyolysis. Therefore, it is necessary to discover drugs with new mechanisms to improve the therapeutic effect on cardiovascular diseases caused by atherosclerosis.

Current studies have shown that the inflammatory response promoted by NLRP3 (NOD-like receptor thermal protein domain associated protein 3) inflammasome is closely related to the pathogenesis of atherosclerosis, thus inhibition of NLRP3 and vascular inflammation provides a new therapeutic approach for cardiovascular diseases caused by atherosclerosis. NLRP3, a protein complex, is an important component of the innate immune system. NLRP3 can recognize molecular patterns associated with a variety of pathogens, and has attracted lots of attention on its role in the pathogenesis of atherosclerosis (Guo, H., et al., Inflammasomes: mechanism of action, role in disease, and therapeutics. Nature medicine, 2015. 21(7): 677-687.). In human, stimulation of NLRP3 inflammasome and subsequent release of interleukin-113 (IL-1(3) are strongly associated with the risk of coronary artery disease (Paramel Varghese, G., et al., NLRP3 Inflammasome Expression and Activation in Human Atherosclerosis. Journal of the American Heart Association, 2016. 5(5)). Inhibition of IL-1β by its monoclonal neutralizing antibodies attenuates atherosclerosis in $ApoE^{-/-}$ mice, while elevated IL-1β level accelerates atherosclerosis in mice and humans (Olofsson, P. S., et al., A functional interleukin-1 receptor antagonist polymorphism influences atherosclerosis development. The interleukin-1beta: interleukin-1 receptor antagonist balance in atherosclerosis. Circulation journal: official journal of the Japanese Circulation Society, 2009. 73(8): 1531-1536.). Abnormal activation of NLRP3 inflammasome and the resulting elevated levels of IL-1β and IL-18 promote foam cell formation and plaque development (Duewell, P., et al., NLRP3 inflammasomes are required for atherogenesis and activated by cholesterol crystals. Nature, 2010. 464(7293): 1357-1361). Results from a Phase III trial of canakinumab developed by Novartis show that neutralizing IL-1β can reduce the recurrence rate of cardiovascular events in patients (Ridker, P. M., et al., Relationship of C-reactive protein reduction to cardiovascular event reduction following treatment with canakinumab: a secondary analysis from the CANTOS randomised controlled trial. Lancet, 2018. 391(10118): 319-328.). Since activation of NLRP3/IL-1β is involved in vascular inflammation and promotes the development of atherosclerosis, inhibition of IL-1β or NLRP3 can delay the development of atherosclerosis. It has been found that several molecular and cellular events can trigger the activation of NLRP3 inflammasome. NF-κB, one of the key transcription factors which participate the inflammation progress, could up-regulate the expression of various inflammatory genes, and it also could activate the NLRP3 inflammasome pathway by inducing transcription of NLRP3 and IL-1β (Qiao, Y., et al., TLR-induced NF-κB activation regulates NLRP3 expression in murine macrophages. FEBS letters, 2012. 586: 1022-1026). In addition to the transcription factor NF-κB, MAPK (P38, ERK, and JNK) signaling pathways are the upstream signals of NLRP3 inflammasome activation and can regulate the expression of IL-1β and pro-inflammatory factors (Quintans, J. S. S., et al., Monoterpenes modulating cytokines—A review. Food and chemical toxicology, 2019. 123, 233-257). Besides, inflammation is related to other diseases such as cancers, so these compounds may also be applied in these diseases.

Dyslipidemia is a key risk factor for atherosclerosis. An increasing number of studies have shown that hypercholesterolemia and degenerated lipids lead to inflammatory responses, which in turn aggravate lipid metabolism disorders (de Jager, S. C., et al., Crosstalk of lipids and inflammation in atherosclerosis: the PRO of PGRN Cardiovascular research, 2013. 100(1): 4-6.). Foam cells secrete pro-inflammatory factors that result in the unlimitedly uptake of degenerated lipids (including cholesterol) by macrophages and vascular smooth muscle cells and the occurrence of vascular inflammation. ATP-binding cassette transporter A1 (ABCA1) and scavenger receptor Class B type I (SR-BI) can mediate the efflux of excess free cholesterol from foam macrophages and vascular smooth muscle cells through cholesterol reversal transport (RCT) by Apolipoprotein A-I (ApoA-I) and high density lipoprotein (HDL) (Zeller, I., et al., Macrophage functions in atherosclerosis. Circulation research, 2014. 115(12): e83-85.). In this way, cholesterol is transported to the liver for recycling or excretion as cholic acid. The promoter region of ABCA1 gene contains multiple binding sites for transcription factors, and the expression of ABCA1 is mainly regulated by the interaction of nuclear receptors (such as peroxisome proliferator activated receptors (PPARs), liver X receptors (LXRs) and retinoid X receptors (RXRs) with specific response elements in the promoter region of ABCA1 (Majdalawieh, A., et al., PPAR-gamma1 and LXR-α face a new regulator of macrophage cholesterol homeostasis and inflammatory responsiveness, AEBP1. Nuclear receptor signaling, 2010. 8: e004.). In addition, AMPK is a master energy regulator of whole-body energy homeostasis. Studies have shown that activation of AMPK increases the protein expression of ABCA1 gene, resulting in increased cholesterol efflux (Wan X., et al., 5'-AMP-activated protein kinase-activating transcription factor 1 cascade modulates human monocyte-derived macrophages to atheroprotective functions in response to heme or metformin Arteriosclerosis, thrombosis, and vascular biology, 2013. 33: 2470-2480.). Taken together, the reduction of foam cells evolved from macrophages and vascular smooth muscle cells in the intima of the vascular wall, the reduction of plasma cholesterol lipids, and the prevention and alleviation of inflammation, are important methods for the treatment of atherosclerosis.

Rutaecarpine (RUT) is an alkaloid derived from the extract of *Tetradium ruticarpum*, which has pharmacological effects of regulating lipid metabolism, anti-oxidation, anti-inflammation and anti-atherosclerosis. Our previous study shows that RUT inhibits atherosclerosis and promotes RCT mainly by upregulating the expression of ABCA1 and the scavenger receptor SR-BI/CLA-1 (CD36 and LIMPII analogous 1, human SR-BI) (Xu, Y., et al., Rutaecarpine suppresses atherosclerosis in $ApoE^{-/-}$ mice through upregulating ABCA1 and SR-BI within RCT. Journal of lipid research, 2014. 55(8): 1634-1647.). We also have found that RUT reduces the levels of some inflammatory factors in serum from $ApoE^{-/-}$ mice induced by high fat diet (HFD) (ZL201110067053.1). However, RUT has a very low oral bioavailability, so we have designed a series of derivatives of RUT (tetrahydroindoloquinazoline compounds) to improve the bioavailability in vivo thereof and maintain the anti-atherosclerosis, anti-inflammatory and other effects thereof in animals.

SUMMARY OF THE INVENTION

Firstly, the present disclosure relates to an indolo[2',3':3,4]pyrido[2,1-b]quinazoline compound represented by general formula (I):

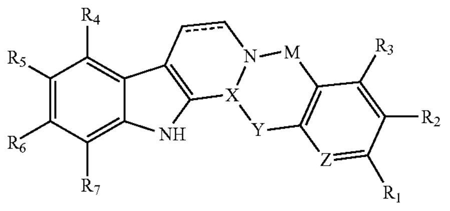

(I)

wherein,

M is C═O or $CH_2$;

Z is CH or N;

X is CH or C;

Y is N, NH, $N^+$, CH, O or N—$R_8$;

$R_1$ to $R_4$ and $R_6$ are H;

$R_5$ is H or halogen atom, and preferably, the halogen atom is F or Cl;

$R_7$ is H, $C_1$-$C_4$ alkyl or halogen atom, and preferably the $C_1$-$C_4$ alkyl is methyl, and the halogen atom is F or Cl;

$R_8$ is H, $C_1$-$C_4$ alkyl or halogenated acetyl, and preferably $R_8$ is methyl or $COCF_3$.

Preferably, the compound has a structure as shown in the following table:

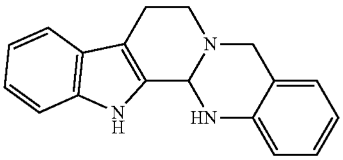

(TR2)

-continued

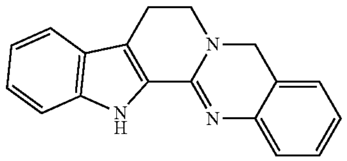 [SMILES: c1ccc2c(c1)CN1CCc3c([nH]c4ccccc34)C1=N2]

(TR3)

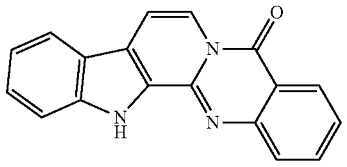 [SMILES: O=c1c2ccccc2nc2c3[nH]c4ccccc4c3ccn12]

(TR4)

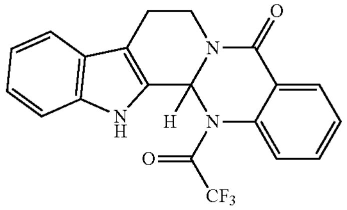 [SMILES: O=C1c2ccccc2N(C(=O)C(F)(F)F)C2c3[nH]c4ccccc4c3CCN12]

(TR6)

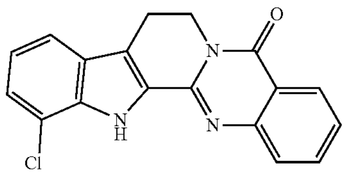 [SMILES: O=c1c2ccccc2nc2n1CCc1c-2[nH]c2c(Cl)cccc12]

(TR10)

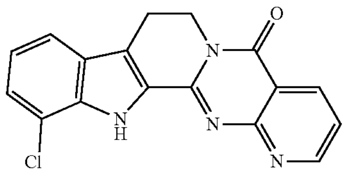 [SMILES: O=c1c2cccnc2nc2n1CCc1c-2[nH]c2c(Cl)cccc12]

(TR11)

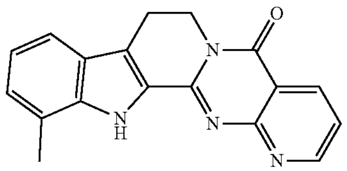 [SMILES: O=c1c2cccnc2nc2n1CCc1c-2[nH]c2c(F)cccc12]

(TR12)

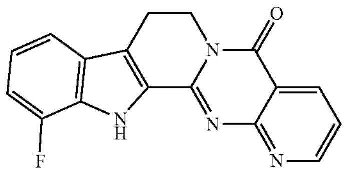

(TR13)

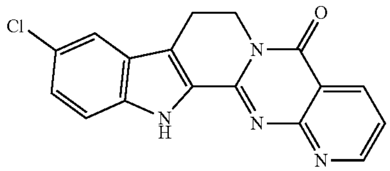 [SMILES: O=c1c2cccnc2nc2n1CCc1c-2[nH]c2ccc(Cl)cc12]

(TR14)

-continued

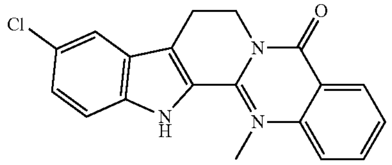

(TR16)

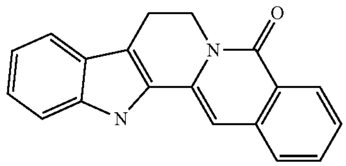 [SMILES: O=c1c2ccccc2cc2n1CCc1c-2[nH]c2ccccc12]

(TY3)

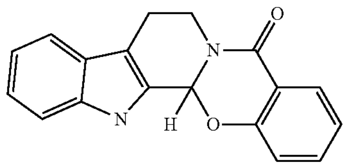 [SMILES: O=C1c2ccccc2OC2c3[nH]c4ccccc4c3CCN12]

(TY4)

The present disclosure further relates to a method for preparing the compound represented by the general formula (I).

In particular, the method for preparing compounds TR2 and TR3 comprises the steps of:

adding rutaecarpine into dry tetrahydrofuran (THF), adding $LiAlH_4$ at room temperature slowly to produce a mixture, and then stirring the mixture for 6-12 h at room temperature for reaction;

quenching the reaction with chlorohydric acid (HCl) aq, filtering the mixture under reduced pressure to get a residue and a filtrate, then washing the residue with DCM ($CH_2Cl_2$) and $CH_3OH$, and collecting the filtrate; and concentrating the filtrate by evaporating most solvent, adjusting the filtrate to a pH of 8-9, extracting the filtrate with DCM to obtain an organic phase and an aqueous phase, combining and concentrating the two phases to obtain a crude product, and purifying the crude product by silica gel column chromatography to obtain compounds TR2 and TR3.

The method for preparing compound TR4 comprises the steps of:

dissolving rutaecarpine in 1,4-dioxane to result in a rutaecarpine solution, heating the rutaecarpine solution to 80° C., adding a solution of DDQ (2,3-dichloro-5,6-dicyano-p-benzoquinone) dissolved in 1,4-dioxane dropwise to the rutaecarpine solution to result in a mixture, refluxing the mixture for 4 h, and concentrating the mixture by evaporating solvent to obtain a residue; and washing the residue with 10% potassium hydroxide (KOH) aq, filtering the residue for multiple times to remove DDQ-2H, washing the residue with 10% HCl aq and $H_2O$ sequentially, filtering the residue under reduced pressure, drying and washing the residue with DCM to obtain compound TR4.

The synthetic route for compounds TR2, TR3 and TR4 is as follows:

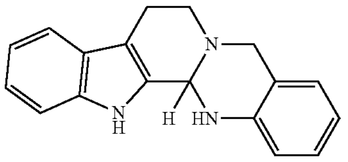

+

TR2

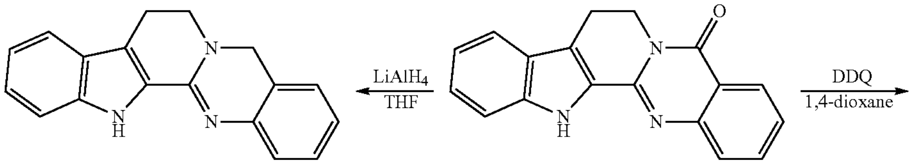

TR3

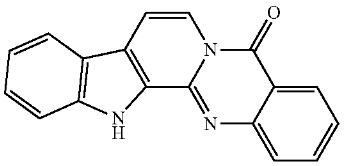

TR4

The method for preparing compound TR6 comprises the steps of:

adding trifluoroacetic anhydride (TFAA) in methyl cyanide (MeCN) dropwise to a solution of 3-(2-(1H-indol-3-yl)-ethyl)-quinazolin-4(3H)-one (T-C1) suspended in MeCN in an ice-water bath, so as to result in a mixture, and allowing the mixture to continue to react for 2 h; and filtering the reacted product solution to obtain a white solid, and purifying the white solid by silica gel column chromatography to obtain compound TR6.

The synthetic route for compound TR6 is as follows:

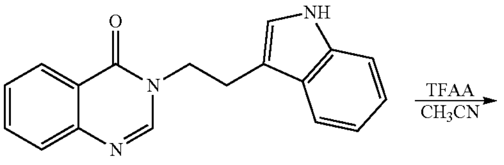

T-C1

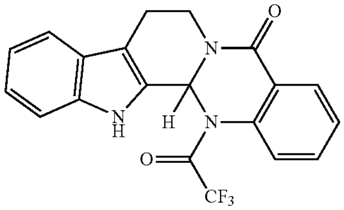

TR6

The method for preparing compounds TR10, TR11, TR12, TR13, TR14 and TR16 comprises the steps of:

dissolving substrate A in toluene to obtain a solution, heating the solution to 80° C., adding phosphorus oxychloride ($POCl_3$) dropwise to the solution, refluxing the solution for 30 min, adding substrate B for reaction, and purifying target products after the reaction completed;

wherein substrate A is 8-chloro-2,3,4,9-tetrahydro-1H-pyrido[3,4-b]indol-1-one;

compound TR10 is obtained where substrate B is 2-aminobenzoic acid;

compounds TR11, TR12, TR13 and TR14 are obtained where substrate B is 2-aminonicotinic acid; and compound TR16 is obtained where substrate B is 2-(methylamino)benzoic acid.

The synthetic route of TR10, TR11, TR12, TR13, TR14 and TR16 is as follows:

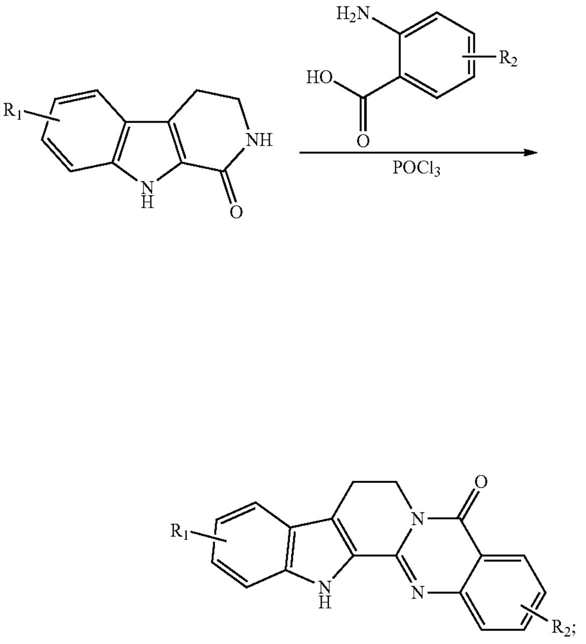

The method for preparing compound TY3 comprises the steps of:

adding triethylamine to a solution of 1-methyl-4,9-dihydro-3H-pyrido[3,4-b]indole in DCM at 0° C., adding 2-iodobenzoyl chloride dropwise to obtain a mixture, allowing the mixture to react for 1 h at 0° C., and filtering the mixture to obtain a crude product as solid;

dissolving the crude product in DMF, adding palladium acetate ($Pd(OAc)_2$), triphenylphosphine ($(Ph)_3P$), potassium acetate (KOAc) and tetra-n-butyl ammonium iodide ($(n\text{-}Bu)_4NI$) sequentially to result in a further mixture, refluxing the further mixture for 8 h under $N_2$, concentrating the further mixture by evaporating most solvent, washing the further mixture with water, extracting the further mixture with AcOEt to obtain an organic phase, and drying the organic phase; and purifying the organic phase by silica gel column chromatography using AcOEt:PE=1:3 as an eluent to obtain compound TY3.

The method for preparing compound TY4 comprises the steps of:

adding 2-hydroxybenzoyl chloride dropwise to a solution of 3,4-dihydro-β-carboline alkaloid (IE-1) dissolved in dry DCM under catalysis of triethylamine to result in a mixture, and subjecting the mixture to reaction for 3 h at room temperature; and washing the mixture with $H_2O$, extracting the mixture with DCM to obtain an organic phase, drying the organic phase, and purifying the organic phase by silica gel column chromatography using AcOEt:PE=1:3 as an eluent to obtain compound TY4.

The synthetic routes of TY3 and TY4 are as follows:

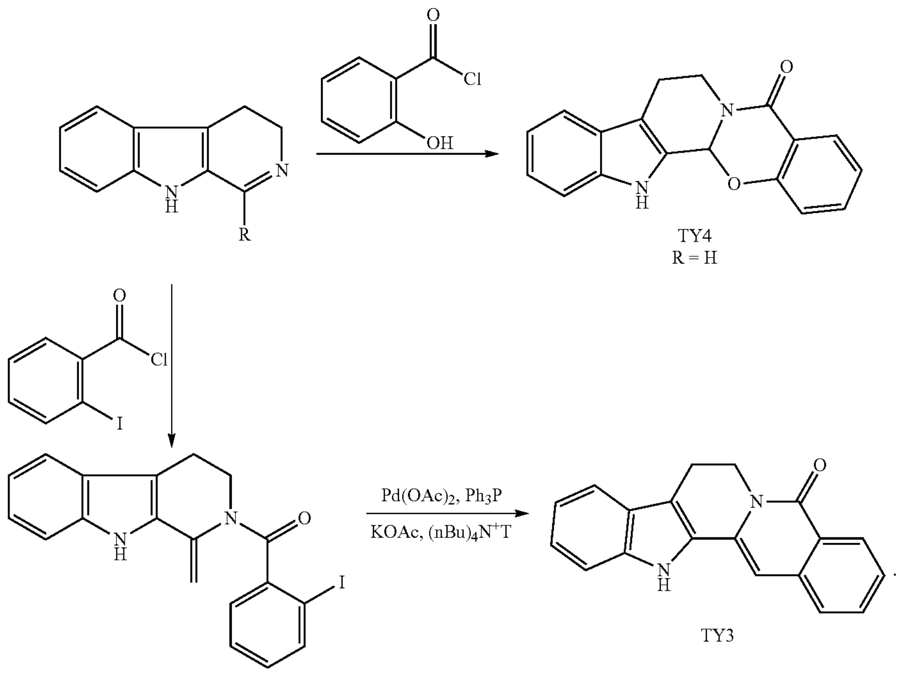

TY4
R = H

TY3

The present disclosure further relates to use of the indolo[2',3':3,4]pyrido[2,1-b]quinazoline compound represented by the general formula (I) in the manufacture of (1) a medicament for treating a cardiovascular and cerebrovascular disease;

(2) a formulation for increasing the expression of AMPK, ABCA1 and SR-BI;

(3) a formulation for activating nuclear receptors (NRs), and inhibiting activity of NLRP3, IL-1β, NF-κB and MAPKs;

(4) a formulation for promoting cellular cholesterol efflux; or (5) a medicament for anti-inflammation.

The cardiovascular and cerebrovascular disease refers to hyperlipidemia, atherosclerosis, myocardial infarction or cerebral apoplexy.

The present disclosure further relates to a pharmaceutical composition comprising a therapeutically effective amount of the indolo[2',3':3,4]pyrido[2,1-b]quinazoline compound represented by general formula (I), and one or more pharmaceutically acceptable carriers.

DETAILED DESCRIPTION OF THE EMBODIMENTS

Figure 1:
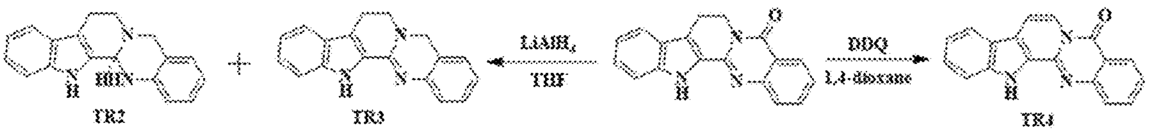
FIG. 1 shows the synthetic route of indolo[2',3':3,4]pyrido[2,1-b]quinazoline compounds described in the present disclosure.
Figure 1:
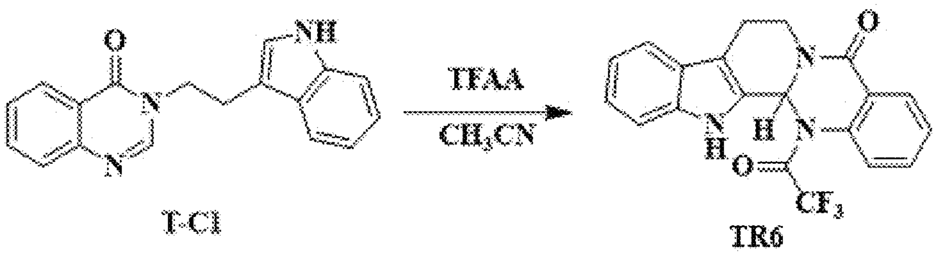
Figure 1:
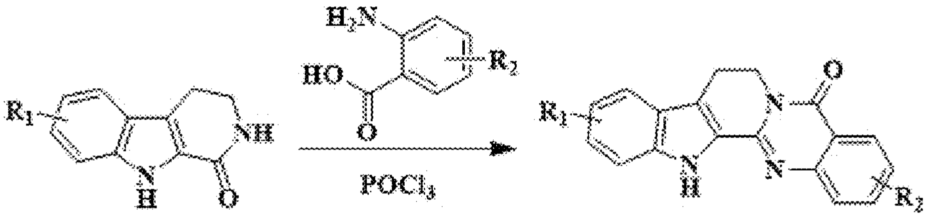
Figure 1:
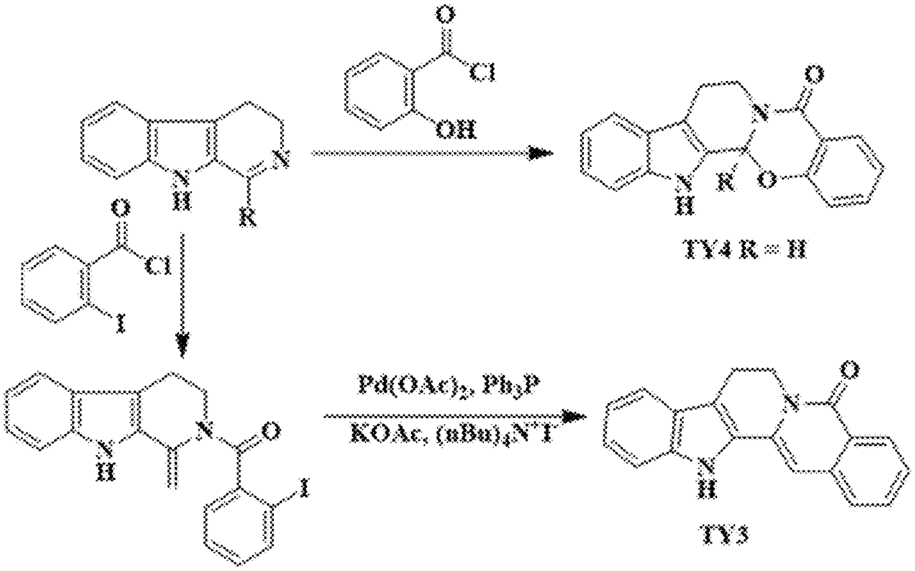

Example 1: Synthesis of TR2 and TR3

Add Rutaecarpine (2.0 g, 7 mmol) into dry THF (100 mL). $LiAlH_4$ (1.06 g, 28 mmol) was then slowly added into the rutaecarpine solution in batches to produce a mixture at room temperature (RT), and then stirring the mixture for 8 h at RT (the yellow reaction mixture turned green along with the heat releasing). The reaction mixture was quenched with HCl aq (1M) and then filtered under reduced pressure. The filter cake was washed with DCM and MeOH, and the filtrate was collected. After evaporating most solvent from the filtrate, the filtrate was adjusted to a pH of 8-9 and then extracted with DCM to obtain an organic phase and an aqueous phase. The two phases were combined, concentrated and purified by silica gel column chromatography using AcOEt:PE=1:4 as an eluent to obtain pure compounds TR2 and TR3.

5,7,8,13,13b,14-hexahydroindolo[2',3':3,4]pyrido[2,1-b]quinazoline (TR2)

(TR2)

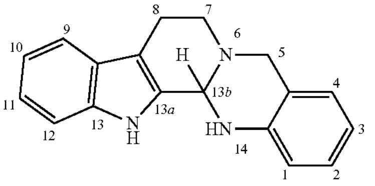

TR2 (16 mg, relative yield 3%), mp 181-183° C. MS (ESI m/z) 276.21 $(M+H)^+$, $^1H$ NMR (400 MHz, $CD_3COCD_3$) δ 10.05 (s, 1H, 13-NH), 7.46 (d, J=8.0 Hz, 1H, 9-H), 7.39 (d, J=8.0 Hz, 1H, 12-H), 7.09 (t, J=7.2 Hz, 1H, 11-H), 7.01 (t, J=7.2 Hz, 1H, 10-H), 6.98-6.95 (m, 2H, 1,2-2H), 6.69-6.66 (m, 2H, 3,4-2H), 5.09 (s, 1H, 14-NH), 4.99 (d, J=4.8 Hz, 1H, 13b-H), 4.05 (d, J=15.2 Hz, 1H, $7-CH_2$—Ha), 3.88 (d, J=15.2 Hz, 1H, $7-CH_2$—Ha'), 3.24-3.19 (m, 2H, $5-CH_2$), 2.89-2.70 (m, 2H, $8-CH_2$—Hb and $8-CH_2$—Hb').

5,7,8,13-tetrahydroindolo[2',3':3,4]pyrido[2,1-b]quinazoline (TR3)

(TR3)

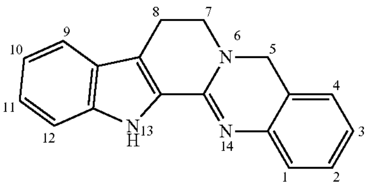

TR3 (0.52 g, relative yield 97%), mp 252-254° C. MS (ESI m/z) 274.22 $(M+H)^+$, $^1H$ NMR (400 MHz, $CD_3COCD_3$) δ 10.51 (s, 1H, 13-NH), 7.58-7.55 (m, 2H, 9,12-2H), 7.22 (t, 1H, J=7.6 Hz, 2-H), 7.13 (d, 1H, J=7.2 Hz, 4-H), 7.07 (t, 1H, J=7.6 Hz, 3-H), 7.02-6.97 (m, 3H, 1, 10, 11-3H), 4.50 (s, 2H, $5-CH_2$), 3.50 (t, J=6.8 Hz, 2H, $7-CH_2$), 3.11 (t, J=6.8 Hz, 2H, $8-CH_2$).

Example 2: Synthesis of indolo[2',3':3,4]pyrido[2,1-b]quinazolin-5(13H)-one (TR4)

(TR4)

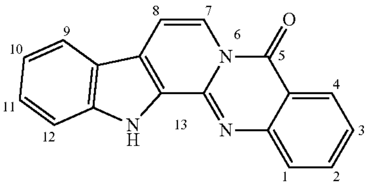

Rutaecarpine (2.0 g, 7 mmol) was dissolved in 1,4-dioxane (20 mL) and heated to 80° C. DDQ (2,3-dichloro-5,6-dicyano-p-benzoquinone) (1.14 g, 5 mmol) dissolved in 1,4-dioxane was added dropwise to the above rutaecarpine solution. The reaction turned green immediately and refluxed for 4 h, and then the mixture was concentrated. The residue was washed and filtered with 10% potassium hydroxide (KOH) aq for multiple times to remove DDQ-2H, and then washed with 10% HCl aq and $H_2O$ sequentially. Then, the solid was filtered under reduced pressure and dried to obtain a crude product. The crude product was then washed with DCM to produce TR4 (0.67 g, yield 47%), a yellow solid. mp 282-284° C. MS (ESI, m/z) 286.17 $(M+H)^+$, 318.30 $(M+Na)^+$.

$^1H$ NMR (400 MHz, DMSO-d6) δ 12.71 (s, 1H, 13-NH), 8.64 (d, J=7.6 Hz, 1H, 4-H), 8.38 (dd, J=1.2, 8.0 Hz, 1H, 9-H), 8.18 (d, J=8.0 Hz, 1H, 7-H), 7.94 (td, 1H, J=1.6, 7.6 Hz, 2-H), 7.86-7.84 (m, 2H, 1,3-2H), 7.69 (d, J=8.0 Hz, 1H, 8-H), 7.50 (qd, 2H, J=1.2, 8.0 Hz, 10,12-2H), 7.30 (dt, 1H, J=0.8, 7.6 Hz, 1H, 11-H).

Example 3: Synthesis of 14-(2,2,2-trifluoroacetyl)-8,13,13b,14-tetrahydroindolo[2',3':3,4]pyrido[2,1-b]quinazolin-5(7H)-one (TR6)

Add trifluoroacetic anhydride (TFAA) in methyl cyanide (MeCN) (0.7 mL, 5 mmol) dropwise to a solution of 3-(2-(1H-indol-3-yl)-ethyl)-quinazolin-4(3H)-one (T-C1) (1.45 g, 5 mmol) suspended in MeCN in an ice-water bath (the temperature was controlled to be lower than 2° C.) until the reaction immediately turns clear. After stirring for 2 h, a white solid was precipitated. Then the white solid was filtered and purified by silica gel column chromatography using AcOEt:PE=1:4 as an eluent to obtain pure compound TR6.

(TR6)

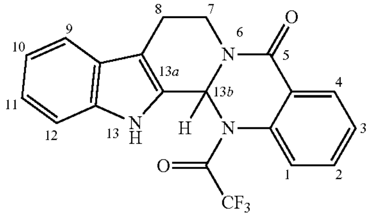

TR6 (0.63 g), mp 199-201° C. HRMS (ESI m/z) calcd $[M+H]^+$ for $C_{20}H_{13}O_2N_3F_3$ 384.1033. found 385.1637.

$^1H$ NMR (500 MHz, DMSO-d6) δ 11.41 (s, 1H, 13-NH), 7.90 (d, J=7.5 Hz, 1H, 4-H), 7.67 (t, J=7.5 Hz, 1H, 3-H), 7.38 (t, J=7.5 Hz, 2H, 2,9-2H), 7.29 (d, J=8.0 Hz, 1H, 12-H), 7.09 (td, J=1.0, 7.5 Hz, 2H, 10,11-H), 6.98 (td, J=1.0, 7.5 Hz, 1H, 1-H), 4.71 (dd, J=5.0, 13.5 Hz, 1H, $CH_2a$), 3.76 (m, 1H, $CH_2a'$), 2.98 (m, 1H, $CH_2b$), 2.64 (dd, J=5.0, 16.0 Hz, 1H, $CH_2b'$).

Example 4: Synthesis of 12-chloro-8,13-dihydroindolo[2',3':3,4]pyrido[2,1-b]quinazolin-5(7H)-one (TR10)

A crude product was obtained via the reaction of 8-chloro-2,3,4,9-tetrahydro-1H-pyrido[3,4-b]indol-1-one (0.44 g, 2 mmol) with 2-aminobenzoic acid (0.27 g, 2 mmol), and then purified to obtain a pure product, namely TR10 (0.28 g, yield 44%), mp 205-208° C., MS (ESI m/z) 322.18$(M+H)^+$.

(TR10)

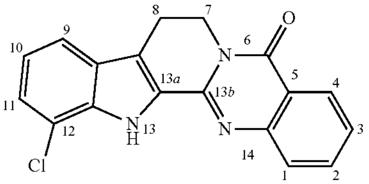

$^1$H NMR (400 MHz, $CD_3COCD_3$) δ 10.97 (s, 1H, 13-NH), 8.22 (dd, J=1.2, 8.0 Hz, 1H, 4-H), 7.78 (td, J=1.6, 7.6 Hz, 1H, 3-H), 7.69 (d, J=8.0 Hz, 1H, 1-H), 7.62 (d, J=8.0 Hz, 1H, 9-H), 7.47 (td, 1H, J=1.2, 8.0 Hz, 2-H), 7.37 (d, J=7.6 Hz, 1H, 11-H), 7.16 (t, J=8.0 Hz, 1H, 10-H), 4.55 (t, J=6.8 Hz, 2H, 7-$CH_2$), 3.28 (t, J=6.8 Hz, 2H, 8-$CH_2$).

Example 5: Synthesis of 12-chloro-8,13-dihydropyrido[2",3":4',5']pyrimido[1',2':1,2]pyrido[3,4-b]indol-5(7H)-one (TR11)

A crude product was obtained via the reaction of 8-chloro-2,3,4,9-tetrahydro-1H-pyrido[3,4-b]indol-1-one (0.40 g, 1.8 mmol) with 2-aminonicotinic acid (0.25 g, 1.8 mmol) and then purified to obtain a pure product, namely TR11 (0.29 g, yield 50%). mp>280° C. MS (ESI m/z) 323.14 $(M+H)^+$.

(TR11)

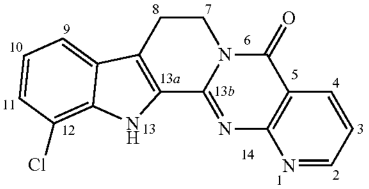

$^1$H NMR (500 MHz, DMSO-d6) δ 12.37 (s, 1H, 13-H), 8.98 (dd, J=2.07, 4.49 Hz, 1H, 2-H), 8.62 (dd, J=1.96, 7.80 Hz, 1H, 4-H), 7.71 (d, J=8.05 Hz, 1H, 9-H), 7.56 (td, J=3.86, 7.56 Hz, 1H, 3-H), 7.41 (d, J=7.48 Hz, 1H, 11-H), 7.15 (t, J=7.52 Hz, 1H, 10-H), 4.48 (t, J=6.91 Hz, 2H, 7-$CH_2$), 3.24 (t, J=6.86 Hz, 2H, 8-$CH_2$).

Example 6: Synthesis of 12-methyl-8,13-dihydropyrido[2",3": 4',5']pyrimido[1',2':1,2]pyrido[3,4-b]indol-5(7H)-one (TR12)

A crude product was obtained via the reaction of 8-methyl-2,3,4,9-tetrahydro-1H-pyrido[3,4-b]indol-1-one (0.30 g, 1.5 mmol) with 2-aminonicotinic acid (0.25 g, 1.8 mmol) and then purified to obtain a pure product, namely TR12 (0.17 g, yield 37%). mp>280° C. MS (ESI m/z) 303.14 $(M+H)^+$.

(TR12)

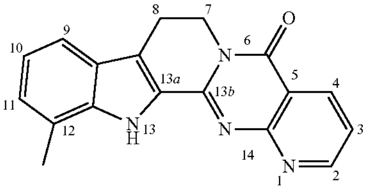

$^1$H NMR (500 MHz, DMSO-d6) δ 11.95 (s, 1H, 13-NH), 8.95 (dd, J=2.06, 4.59 Hz, 1H, 2-H), 8.54 (dd, J=2.01, 7.85 Hz, 1H, 4-H), 7.54-7.46 (m, 2H, 3,9-H), 7.11 (d, J=6.93 Hz, 1H, 11-H), 7.04 (t, J=7.48 Hz, 1H, 10-H), 4.47 (t, J=6.93 Hz, 2H, 7-$CH_2$), 3.21 (t, J=6.89 Hz, 2H, 8-$CH_2$), 2.60 (s, 3H, $CH_3$).

Example 7: Synthesis of 12-fluoro-8,13-dihydropyrido[2",3":4',5']pyrimido[1',2':1,2]pyrido[3,4-b]indol-5(7H)-one (TR13)

A crude product was obtained via the reaction of 8-fluoro-2,3,4,9-tetrahydro-1H-pyrido[3,4-b]indol-1-one (0.41 g, 2 mmol) with 2-aminonicotinic acid (0.28 g, 2 mmol) and then purified to obtain a pure product, namely TR13 (0.17 g, yield 28%). mp>280° C. MS (ESI m/z) 307.18 $(M+H)^+$.

(TR13)

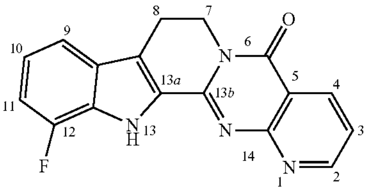

$^1$H NMR (500 MHz, DMSO-d6) δ 12.68 (s, 1H, 13-NH), 8.96 (dd, J=2.00, 4.87 Hz, 1H, 2-H), 8.58-8.51 (m, 1H, 4-H), 7.56-7.46 (m, 2H, 3,9-H), 7.18-7.06 (m, 2H, 10,11-H), 4.48 (t, J=6.94 Hz, 2H, 7-$CH_2$), 3.27-3.16 (m, 2H, 8-$CH_2$).

Example 8: Synthesis of 10-chloro-8,13-dihydropyrido[2",3": 4',5']pyrimido[1',2':1,2]pyrido[3,4-b]indol-5(7H)-one (TR14)

A crude product was obtained via the reaction of 6-chloro-2,3,4,9-tetrahydro-1H-pyrido[3,4-b]indol-1-one (0.44 g, 2 mmol) with 2-aminonicotinic acid (0.28 g, 2 mmol) and then purified to obtain a pure product, namely TR14 (0.06 g, yield 9.3%). mp>280° C. MS (ESI m/z) 321.07 $(M+H)^+$.

(TR14)

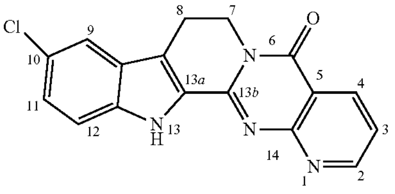

$^1$H NMR (500 MHz, DMSO-d6) δ 12.38 (s, 1H, 13-NH), 8.96 (dd, J=2.02, 4.58 Hz, 1H, 2-H), 8.55 (dd, J=2.03, 7.87 Hz, 1H, 4-H), 7.80 (d, J=1.98 Hz, 1H, 9-H), 7.55-7.47 (m, 2H, 3,12-H), 7.31 (dd, J=2.06, 8.74 Hz, 1H, 11-H), 4.46 (t, J=6.93 Hz, 2H, $CH_2N$—), 3.22 (t, J=7.03 Hz, 2H, $CH_2$).

Example 9: Synthesis of 10-chloro-14-methyl-8,13,13b,14-tetrahydroindolo[2',3':3,4]pyrido[2,1-b]quinazolin-5(7H)-one (TR16)

A solid crude product was obtained via the reaction of 6-chloro-2,3,4,9-tetrahydro-1H-pyrido[3,4-b]indol-1-one (0.33 g, 1.5 mmol) with 2-(methylamino)nicotinic acid (0.227 g, 1.5 mmol) and then recrystallized in MeOH to produce TR16 (0.144 g, yield 29%). mp 242-245° C. MS (ESI, m/z) 336.05 $(M+H)^+$.

(TR16)

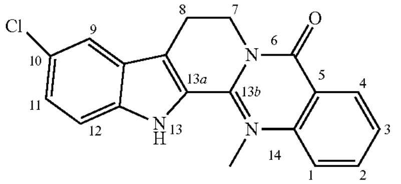

$^1$H NMR (400 MHz, DMSO-d6) δ 12.73(brs, 1H, 13-NH), 8.36 (dd, J=1.2, 8.0 Hz, 1H, 1-H), 8.20 (d, J=8.0 Hz, 1H, 4-H), 8.14 (td, J=1.2, 8.0 Hz, 1H, 3-H), 8.03 (d, J=2.0 Hz, 1H, 9-H), 7.82 (t, J=8.0 Hz, 1H, 2-H), 7.71 (d, J=8.8 Hz, 1H, 12-H), 7.52 (dd, J=2.0, 8.8 Hz, 1H, 11-H), 4.46 (t, J=7.2 Hz, 2H, 7-$CH_2$), 4.36 (s, 3H, $CH_3$), 3.31 (t, J=7.2 Hz, 2H, 8-$CH_2$).

$^{13}$C NMR (100 MHz, DMSO-d6) δ 158.18 (qC), 150.09 (qC), 139.58 (qC), 139.48 (qC), 136.78 (CH), 129.12 (CH), 128.91 (CH), 128.69 (qC), 127.76 (CH), 126.10 (qC), 124.16 (qC), 121.43 (qC), 120.75 (CH), 118.81 (qC), 118.69 (CH), 115.33 (CH), 42.19 ($CH_2$), 40.95 ($CH_3$), 18.41 ($CH_2$).

Example 10: Synthesis of 8,13-dihydroindolo[2',3':3,4]pyrido[1,2-b]isoquinolin-5(7H)-one (TY3)

Triethylamine (TEA) (0.6 mL, 4.3 mmol) was added to a solution of 1-methyl-4,9-dihydro-3H-pyrido[3,4-b]indole (0.75 g, 4 mmol) in DCM (30 mL) at 0° C., and then added 2-iodobenzoyl chloride (0.6 mL, 4 mmol) dropwise. After stirring for 1 h at 0° C., a solid was precipitated. Then the solid was filtered and dried to obtain a crude product (1.8 g). The crude product (0.8 g, 2 mmol) was dissolved in DMF and then added with palladium acetate ($Pd(OAc)_2$) (30 mg, 0.15 mmol), triphenylphosphine ($(Ph)_3P$) (100 mg, 0.4 mmol), potassium acetate (KOAc) (0.78 g, 8 mmol) and tetra-n-butyl ammonium iodide ($(n\text{-}Bu)_4NI$) (0.8 g, 2 mmol) successively. After refluxing for 8 h under $N_2$, the mixture was concentrated by evaporating most solvent, washed with $H_2O$, and then extracted with AcOEt. The organic phase was concentrated and purified by silica gel column chromatography using EtOAc:PE=1:3 as a eluent to obtain compound TY3 (60 mg, yield 11%). mp 307-310° C. MS (ESI m/z) 287.16 $(M+H)^+$, 284.96 $(M-H)^+$.

(TY3)

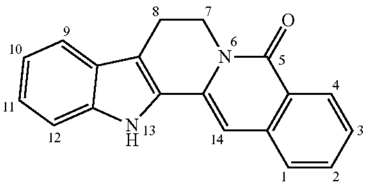

$^1$H NMR (400 MHz, DMSO-d6) δ 11.70 (s, 1H, 13-NH), 8.25 (d, J=8.0 Hz, 1H, 1-H), 7.72 (td, J=1.2, 8.0 Hz, 1H, 2-H), 7.64-7.59 (m, 2H, 9-H and 4-H), 7.49-7.43 (m, 2H, 12-H and 14-H), 7.22 (td, J=0.8, 8.0 Hz, 1H, 3-H), 7.10-7.06 (m, 2H, 10,11-2H), 4.41 (t, J=6.8 Hz, 2H, 7-$CH_2$), 3.10 (t, J=6.8 Hz, 2H, 8-$CH_2$).

Example 11: Synthesis of 7,8,13,13b-tetrahydro-5H-benzo[5',6'][1,3]oxazino[3',2':1,2]pyrido[3,4-13]indol-5-one (TY4)

2-hydroxybenzoyl chloride (0.40 g, 2.6 mmol) was added dropwise to a solution of IE-1 (0.34 g, 2 mmol) in dry DCM under catalysis of TEA (0.50 mL, 2 mmol). After stirring for 3 h at RT, the mixture was washed with $H_2O$ and extracted with DCM. The organic phase was concentrated and purified by silica gel column chromatography (EtOAc:PE=1:3) to obtain compound TY4 (0.12 g, yield 20.7%). mp 228-229° C. MS (ESI m/z) 291.12 $(M+H)^+$, 313.06 $(M+Na)^+$.

(TY4)

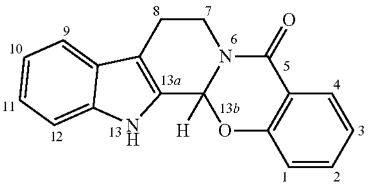

$^1$H NMR (500 MHz, DMSO-d6) δ 11.52 (s, 1H, 13-H), 7.92 (d, J=7.5 Hz, 1H, 1-H), 7.62-7.58 (m, 2H, 9-H and 2-H), 7.44 (d, J=8.5 Hz, 1H, 4-H), 7.25-7.19 (m, 2H, 11,12-2H) 7.15 (d, J=8.0 Hz, 1H, 3-H), 7.08 (t, J=7.5 Hz, 1H, 10-H), 6.69 (s, 1H, 13b-H), 4.74 (dd, J=4.0, 13.0 Hz, 1H, 7-$CH_2$—Ha), 3.23 (td, 1H, J=4.0, 12.0 Hz, 7-$CH_2$—Ha'), 2.97-2.83 (m, 2H, $CH_2$).

Example 12: Up-Regulation of ABCA1 and SR-BI by the Compounds of the Disclosure

Experiments were conducted to detect whether the compounds of the disclosure can pharmacologically up-regulate the expression of ABCA1 and SR-BI. Firstly, ABCA1P-LUC HepG2 cells or SR-BI-LUC HepG2 cells in logarithmic growth phase were digested, diluted in cell culture medium, and counted. Cells were seeded into 96-well plates at a density of $5\times10^5$/ml (100 μL of the single-cell suspension per well). After cells fully adhered (about 6 h), the medium containing 10% FBS was removed, and the cells were gently washed with PBS. Serum free MEM-EBSS medium (200 μL per test well) and 2 μL of the compounds to be tested (at a final concentration of 10 μg/mL) were added to each test well, and meanwhile, DMSO at a corresponding concentration was added to the control well. After 18-24 h, the medium was removed. Cell Luciferase activity was measured by a method as described in the Luciferase Assay System. By optimizing the final concentration of DMSO, the treatment time of the compounds on the cells and the number of cells seeded into each well during the screening, the final screening conditions were determined as follows: each well is seeded with $5\times10^4$ cells, DMSO is added at a final concentration of 1%, and the sample is treated for 18 h.

The ratio of change of luciferase activity is calculated with the following formula:

$$\text{Ratio of change (\%)} = A/B \times 100;$$

wherein A is the luciferase activity (RLU) measured after the compound to be tested is added, and B is the luciferase activity (RLU) measured after the blank control (DMSO) is added. The luciferase activity of cells in each well was measured, and the dose-effect relationship between the concentration of the compound and the ratio of change of the luciferase activity was determined to calculate the $EC_{50}$.

TABLE 1
ABCA1 and SR-BI expression activity of series compounds
| code | compd | ABCA1 | | SR-BI | |
| --- | --- | --- | --- | --- | --- |
| | | $EC_{50}$ | max | $EC_{50}$ | max |
| RUT | 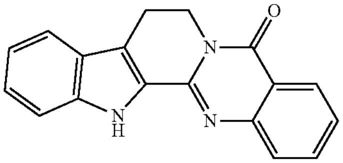 | 0.115 | 2.09 | 0.094 | 2.12 |
| TR2 | 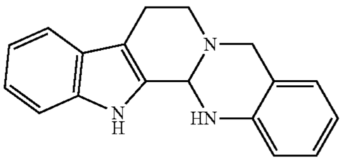 [SMILES: c1ccc2c(c1)CN1CCc3c([nH]c4ccccc34)C1N2] | 0.193 | 1.66 | 0.338 | 1.76 |
| TR3 | 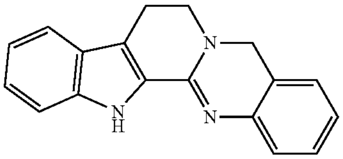 [SMILES: c1ccc2c(c1)CN1CCc3c([nH]c4ccccc34)C1=N2] | 0.025 | 2.26 | 0.074 | 2.07 |
| TR4 | 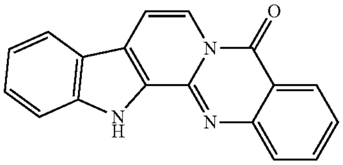 [SMILES: O=c1c2ccccc2nc2c3[nH]c4ccccc4c3ccn12] | 0.031 | 1.84 | 0.019 | 1.74 |
| TR6 | 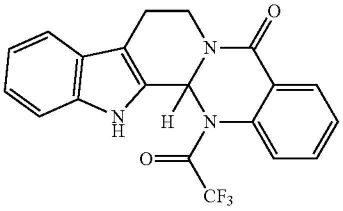 [SMILES: O=C1c2ccccc2N(C(=O)C(F)(F)F)C2c3[nH]c4ccccc4c3CCN12] | 0.074 | 1.96 | 0.033 | 1.56 |
| TR10 | 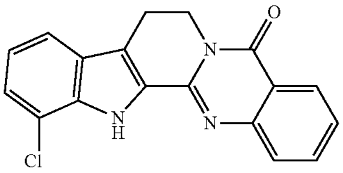 [SMILES: O=c1c2ccccc2nc2n1CCc1c-2[nH]c2c(Cl)cccc12] | 0.239 | 1.43 | 0.363 | 1.72 |
| TR11 | 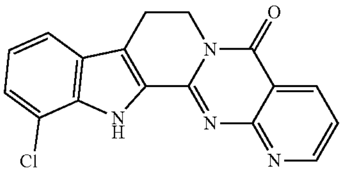 | 0.108 | 1.57 | 0.236 | 1.68 |
| TR12 | 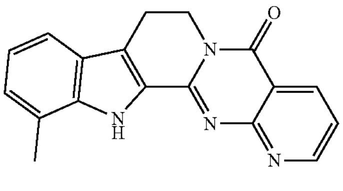 [SMILES: Cc1cccc2c3c([nH]c12)-c1nc2ncccc2c(=O)n1CC3] | 0.068 | 1.51 | 0.124 | 1.44 |

TABLE 1-continued

ABCA1 and SR-BI expression activity of series compounds

| | | ABCA1 | | SR-BI | |
|---|---|---|---|---|---|
| code | compd | $EC_{50}$ | max | $EC_{50}$ | max |
| TR13 | 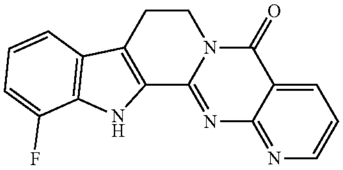 | 0.304 | 1.54 | 0.478 | 1.72 |
| TR14 | 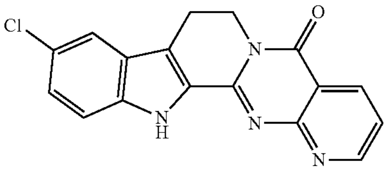 [SMILES: O=c1c2cccnc2nc2n1CCc1c-2[nH]c2ccc(Cl)cc12] | 0.943 | 1.48 | 0.751 | 1.57 |
| TR16 | 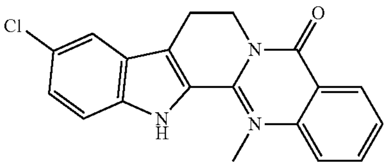 | — | | 1.579 | 1.27 |
| TY3 | 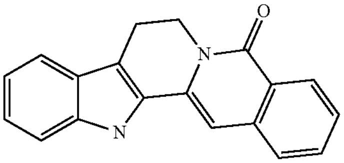 [SMILES: O=c1c2ccccc2cc2n1CCc1c-2[nH]c2ccccc12] | 0.23 | 1.97 | 2.502 | 1.41 |
| TY4 | 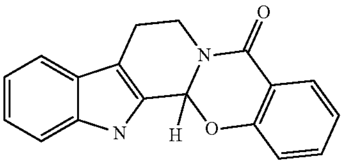 [SMILES: O=C1c2ccccc2OC2c3[nH]c4ccccc4c3CCN12] | 1.585 | 1.5 | 0.568 | 1.22 |

Example 13: Detection of the Transient Transfection Activity of Nuclear Receptor Reporter Gene (pBIND-hPPARs/LXRs-LBD)

HepG2 cells in logarithmic growth phase were digested, seeded into the white/clear 96-well plate at a density of $5\times10^4$ cells/well/100 μL until the cells grew to about 90% confluence and in good condition. 0.5 μL liposome (Lipofectamine® 2000) diluted with blank medium to 25 μL per well and incubated at room temperature for 5 min. The corresponding plasmids DNA (nuclear receptor plasmid: Gal4=1:10) were diluted in blank DMEM medium to 25 μL/well (mixing of two plasmids), then mixed evenly with the diluted liposome, and incubated for 20 min at 37° C. The DNA-liposome complex (50 μL per well) was added with the DMEM complete medium (100 μL per well) and mixed thoroughly to obtain a DNA-liposome complex cell culture. The cell medium was discarded, and replaced with the DNA-liposome complex cell culture (150 μL/well) (37° C., 5% $CO_2$). After 6 h, the DNA-liposome complex cell culture medium was discarded, and 200 μL serum-free DMEM medium containing the compound at an appropriate concentration was added to each test well, and cultured for 18-24 h. The cell Luciferase activity was measured by the method as described in the Luciferase Assay System.

The LXRα/β agonist activity of the compounds that significantly up-regulated ABCA1 expression was determined. The results show that compounds TR3, TR4, and TR6 showed agonist activity in both LXRα/β subtypes. According to the $EC_{50}$ and maximum up-regulation fold of these compounds on ABCA1 expression, it is preliminarily determined that compounds TR3, TR4 and TR6 may have effects on both subtypes, as shown in Table 2.

TABLE 2

LXRα/β agonist activity of active compounds

| | LXRα | | LXRβ | |
|---|---|---|---|---|
| Code | $EC_{50}$ | max | $EC_{50}$ | max |
| TR3 | 2.176 | 1.36 | 2.116 | 1.42 |
| TR4 | 0.29 | 1.84 | 0.16 | 1.88 |
| TR6 | 0.01 | 2.03 | 0.019 | 1.69 |

Figure 2:
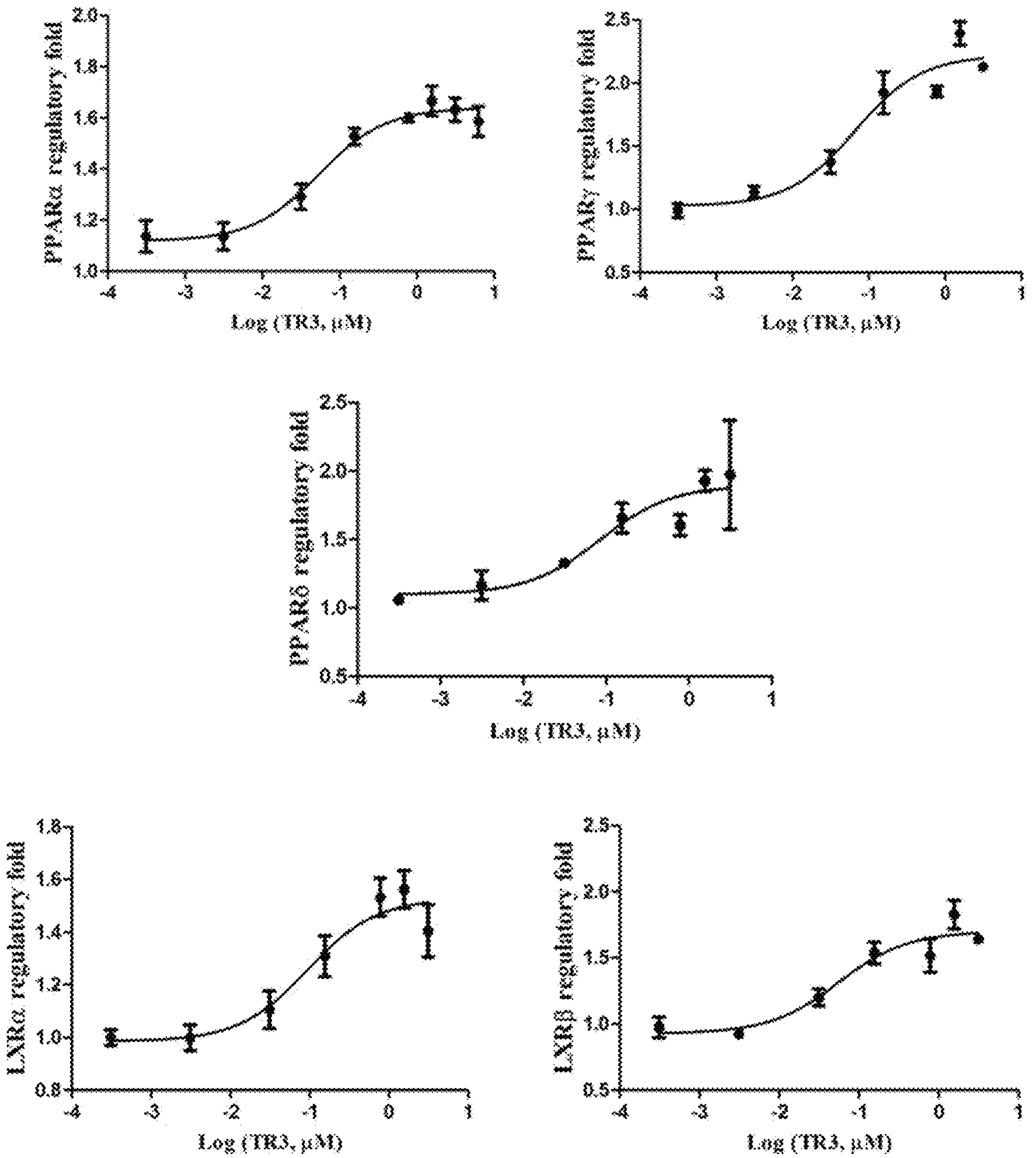
FIG. 2 shows that TR3 activated PPARα/γ/δ and LXRα/β simultaneously.

The results of compound TR3 (marked as R3 in the figure) are shown in FIG. 2. As can be seen, TR3 simultaneously activated PPARα/γ/δ and LXRα/β to a certain extent. However, the up-regulating transcription activity of ABCA1 by TR3 was significantly inhibited when compound R3 was co-incubated with any nuclear receptor inhibitor (PPARα inhibitor—MK886, PPARγ inhibitor—GW9662, PPARδ inhibitor—GSK3787, or LXRα/β inhibitor—GGPP).

Example 14: Inhibition of Development of Atherosclerosis in Apoe$^{-/-}$ Mice on High-Fat Diet by Compound TR3

1. Construction Atherosclerosis Model in Apoe$^{-/-}$ Mice, Administration and Sampling 6-week-old male C57/BL6 ApoE$^{-/-}$ mice were fed on normal chaw diet for one week. The mice were randomly divided into three groups (control group, high-fat diet model group, and treatment group, 12 mice per group) according to the body weight. From 7-week-old, the high-fat diet model group and the treatment group were fed on a high fat diet (HFD) (0.15% cholesterol and 20% fat), and the control group was fed on normal chow diet. The treatment group (R3) mice were administered intragastrically with TR3 (5 mg/kg). The control group and the high-fat diet model group mice were intragastrically administered with sodium carboxymethylcellulose (CMC-Na) solution. After 12 weeks of administration, all mice were fasted overnight. The blood sample was taken from the retro-orbital plexus, collected in a EP tube, and then centrifuged for 15 min (2500 rpm). The centrifuged serum (upper layer) was transferred to new EP tubes (divided into two aliquots) and stored at −20° C. for further use. The mice were fixed, and the skin was cut open along the midline of the abdomen to the neck. The abdominal cavity was cut open to collect the fresh liver tissue. The Liver tissue was put into 3 freezing tubes, and then immediately put into liquid nitrogen for subsequent detection of liver lipid detection and extraction of RNA and protein. The thorax was cut open to expose the heart. The heart was perfused with 10 ml PBS, and then fixed by perfusion with 4% paraformaldehyde solution until the liver turned white. The fixed liver was taken out and placed in a six-well plate containing 4% paraformaldehyde solution for further fixation. The full-length aorta (from the ascending aorta to the common iliac arteries) was isolated and placed in a six-well plate containing 4% paraformaldehyde solution. The aorta was fixed in 4% paraformaldehyde solution overnight and then stored in 20% sucrose solution at 4° C.

2. Dissection and Oil Red Staining of Aortas from Apoe$^{-/-}$ Mice

The aorta was taken out from the 20% sucrose solution and rinsed with PBS. The adipose tissue and other muscle tissue around the aorta were carefully removed from the aorta under an anatomical microscope. The aorta was split longitudinally, rinsed with PBS, immersed in 60% isopropyl alcohol for 2 min for synchronization. The synchronized aorta was put into freshly prepared Oil Red O (ORO) solution for 15 min for staining, 60% isopropyl alcohol for 1 min for color separation, and then PBS solution. The stained aorta was completely spread on a glass slide and placed under an anatomical microscope to capture images.

Figure 3:
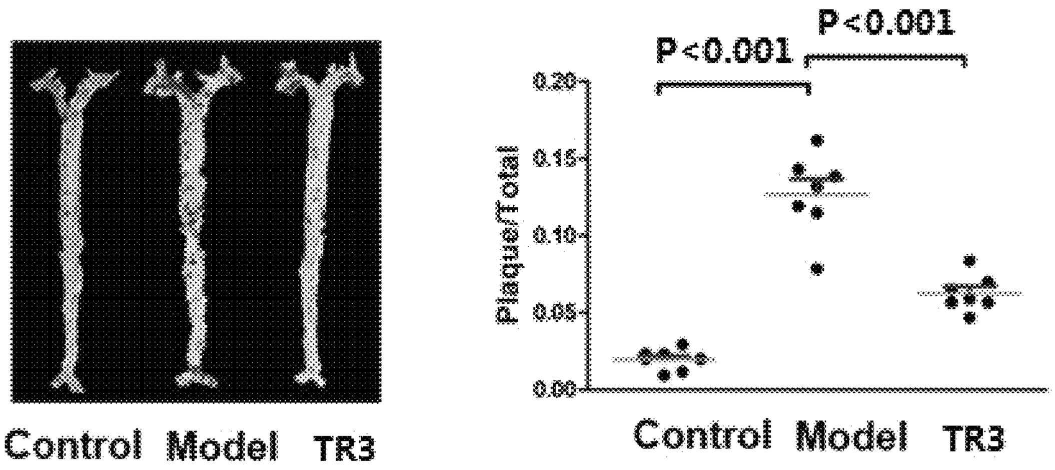
FIG. 3 shows that TR3 inhibited the formation of atherosclerotic plaques.

The results are shown in FIG. 3. As can be seen from the ORO staining of the aorta, as compared with the control group, the plaque area was obviously increased in the model group, indicating that the modeling is successful. As compared with the model group, the atherosclerotic plaque area in the aorta was significantly reduced in the TR3 treatment group. The above results indicate that TR3 has a good inhibition effect on the formation of atherosclerotic plaques, and might be promising in the treatment of atherosclerosis.

3. Measurement of Serum Lipid Levels in Apoe$^{-/-}$ Mice

Figure 4:
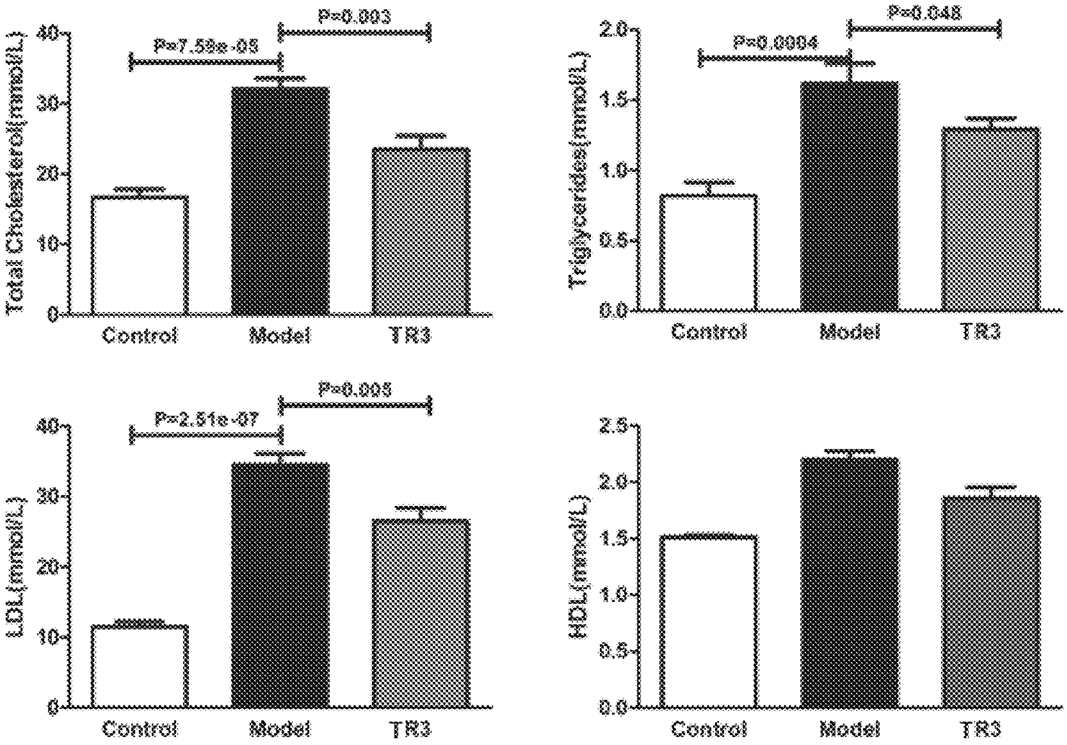
FIG. 4 shows that TR3 significantly lowered the plasma levels of TC, LDL-C and TG in $ApoE^{-/-}$ mice.

The plasma biochemical indices were measured by using commercially available kits (Biosino Bio-technology and Science Inc., China) and the automatic biochemical analyzer. As shown in FIG. 4, the levels of TC, LDL-C and TG were greatly decreased in serum of TR3 treated ApoE$^{-/-}$ mice when compared with that of model group, indicating TR3 could significantly improve hyperlipemia in ApoE$^{-/-}$ mice.

4. Measurement of Serum Inflammatory Factor Levels in Apoe$^{-/-}$ Mice

The levels of IL-1β, IL-18, IL-6, TNF-α and IL-10 in the serum of ApoE$^{-/-}$ mice were measured by using the corresponding ELISA kits (Nanjing Sen Bei Jia Biotechnology Co., Ltd., Nanjing, China). Standard dilution and addition: the standard was diluted by gradient, and 10 wells on the coated ELISA plate were set for standard addition. Sample addition: blank wells and sample wells were set separately. The sample wells of the coated ELISA plates were first added with 40 μL sample diluent, and then added 10 μL sample (the final dilution of the sample is 5-fold). The sample was added to the well bottom of the coated ELISA plates without touching the well wall as far as possible and homogenously mixed by gently shanking the plates. Incubation: the plates were sealed with Closure plate membrane and incubated at 37° C. for 30 min. Washing buffer preparation: the 30-fold concentrated washing buffer was 30-fold diluted with distilled water and stored for further use. Washing: The Closure plate membrane was removed and the liquid was discarded from the plate. The plate was dried by swing. and The washing buffer was added to each well of the plate and allowed to stand for 30 s and then discarded (repeated 5 times), and dried by patting. Enzyme addition: Each well was added with 50 μL HRP-conjugate reagent, except for the blank well. Incubation: this step was the same as the above incubation step 3. Washing: this step was the same as the above washing step 5. Color development: 50 μL chromogen substrate A and then 50 μL chromogen substrate B were added to each well, mixed by gently shaking, and incubated for 15 min at 37° C. in dark. Stopping: each well was added with 50 μL Stop Solution to stop the reaction (the color changed from blue to yellow). Assay detection: the absorbance at 450 nm of each well was read with the absorbance at 450 nm of the blank well as zero, and this process was performed within 15 min after the stop solution was added.

Figure 5:
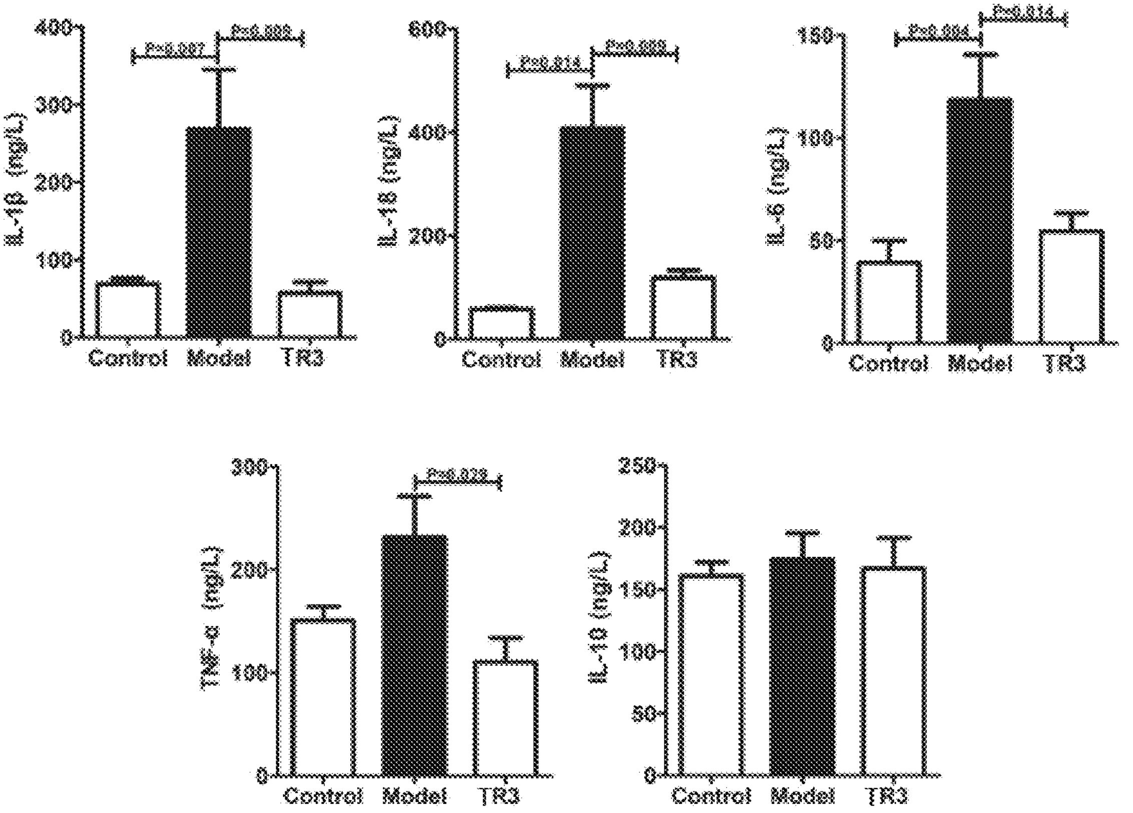
FIG. 5 shows that TR3 lowered the plasma levels of IL-1β, IL-18, IL-6 and TNF-α in $ApoE^{-/-}$ mice.

The results are shown in FIG. 5. As can be seen, TR3 decreased the levels of IL-1β, IL-18 and IL-6 significantly and the level of TNF-α slightly in mouse serum, indicating that TR3 could inhibit the level of inflammatory factors.

5. Measurement of Protein Levels in Liver Tissue of Apoe$^{-/-}$ Mice

When animal tissues were used to prepare protein samples, the tissues were firstly homogenized and lysed in the RIPA lysis buffer. The subsequent steps were the same as those for preparing protein samples from cells. When cell supernatants were used to prepare protein samples, the supernatants were freeze-dried, needed to be extracted using a protein recovery kit (Applygen, Beijing, China), and then analyzed by western-blot.

Figure 6:
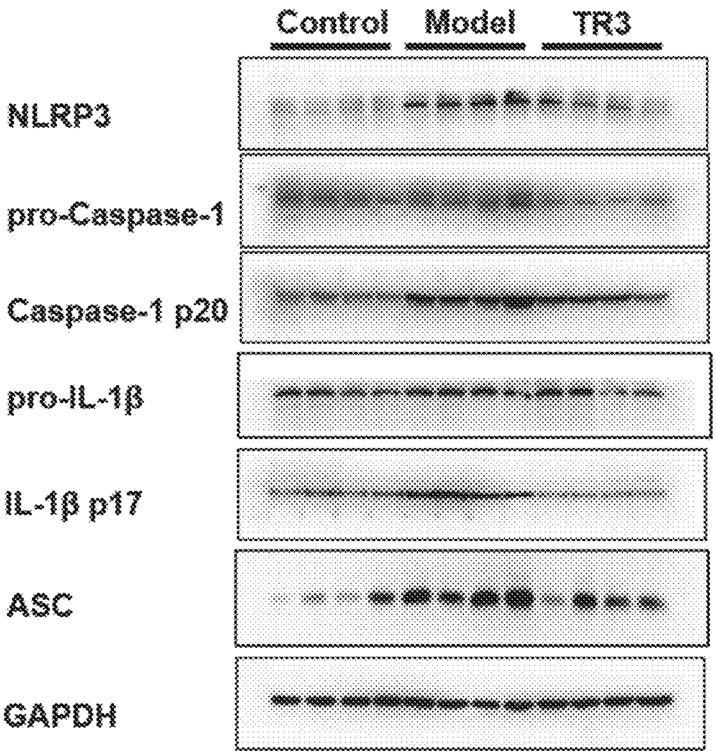
FIG. 6 shows that TR3 significantly inhibited the expression of NLRP3, Caspase-1 and IL-1β.

The western-blot was used to detect the effects of TR3 on the activation of NLRP3 inflammasome and other related proteins in the liver of ApoE$^{-/-}$ mouse and J774A1 cells. As shown in FIG. 6, TR3 significantly inhibited the expression of the proteins such as NLRP3, Caspase-1 and IL-1β.

Figure 7:
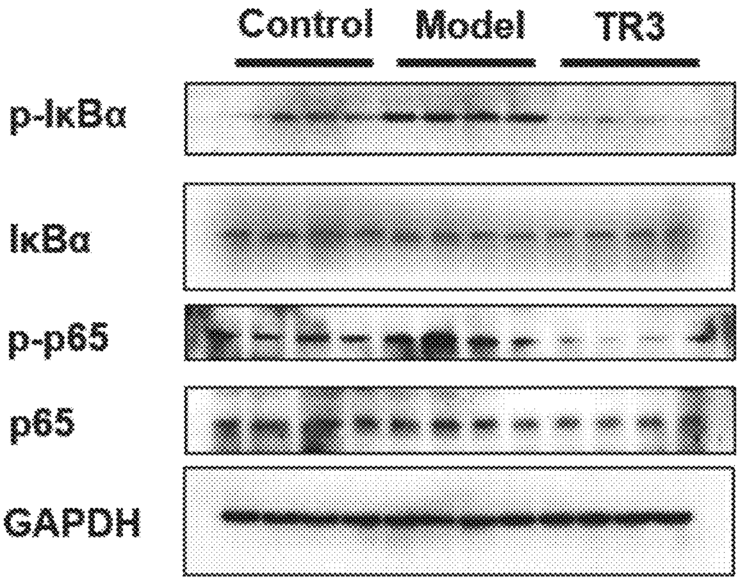
FIG. 7 shows that TR3 significantly inhibited the expression of p-IκBα and p-P65 protein in livers of $ApoE^{-/-}$ mice.
Figure 8:
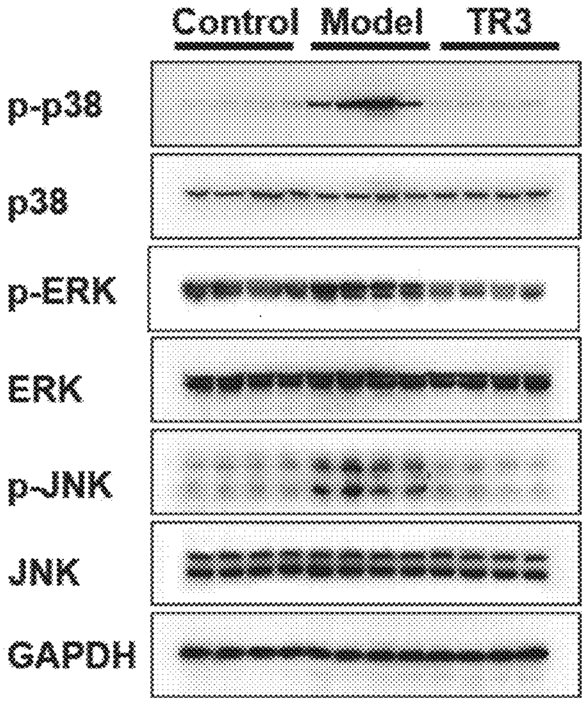
FIG. 8 shows that TR3 inhibited the protein expression of P-P38, P-ERK and P-JNK.

We also examined the effects of TR3 on NF-κB and MAPK signaling pathway in $ApoE^{-/-}$ mice. As shown in FIGS. 7 and 8, TR3 significantly inhibited the expression of p-IκBα and p-P65 in the liver of $ApoE^{-/-}$ mice, indicating that TR3 could inhibit NF-κB signaling pathway. In addition, TR3 also inhibited the expression of p-P38, p-ERK and p-JNK, indicating that TR3 could inhibit MAPK signaling pathway.

Figure 9:
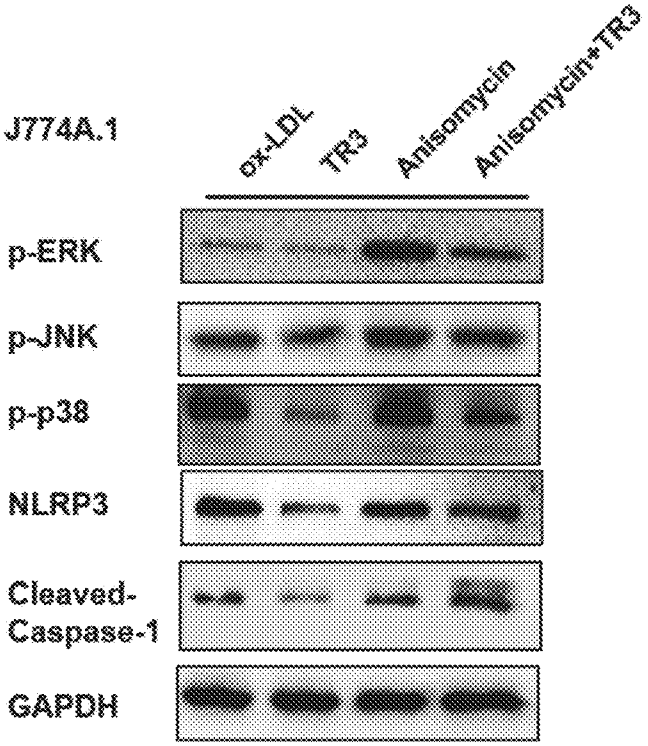
FIG. 9 shows that TR3 inhibited NLRP3 inflammasome activation through MAPK signaling pathway.

After that, the MAPK signaling pathway agonist Anisomycin and TR3 were added into J774A-1 cells. As shown in FIG. 9, the inhibitory effect of TR3 on NLRP3, Caspase-1, and IL-1β was reduced, indicating that compound TR3 inhibits the activation of NLRP3 inflammasome in J774A.1 cells through MAPK signaling pathway.

Figure 10:
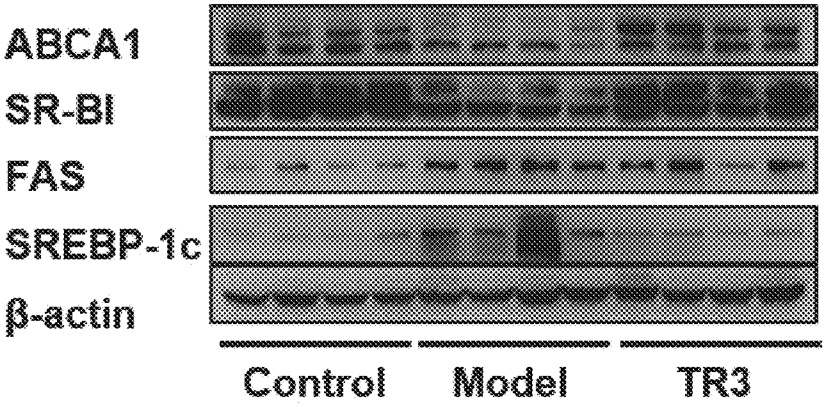
FIG. 10 shows that TR3 increased ABCA1 and SR-BI protein expression in livers of $ApoE^{-/-}$ mice.

Taken together, TR3 significantly inhibited the activation of NLRP3 inflammasome in the liver of $ApoE^{-/-}$ mice, thereby reducing the production of IL-1β. In addition, TR3 increased the expression of ABCA1 and SR-BI in the liver of $ApoE^{-/-}$ mice (FIG. 10).

Example 15: Activation of AMPK by Compound TR3

Murine macrophages RAW 264.7 cells were subcultured about every 48 h. When the cells were approximately 100% confluent, the old culture medium was removed, and the cells were washed with PBS and digested with trypsin at an appropriate amount for about 2 min at RT. After the digestion solution was removed, the RPMI-1640 complete medium containing 10% FBS was added immediately to inhibit the activity of trypsin. The cells in the culture flask were repeatedly and gently blown with a curved straw, so that they were completely detached from the bottom of the flask and dispersed into the single-cell suspension. The cells were seeded into a new cell flask at a density of 1:4-1:6, and added with an appropriate amount of the complete medium. The flask was placed in an incubator and cultured at 37° C., 5% $CO_2$. RAW264.7 cells were pretreated with si-AMPK (AMPK siRNA) for 24 h, and then treated with compound TR3 (1 μM) for 24 h. The expression of ABCA1 and AMPK was detected by western-blot.

Figure 11:
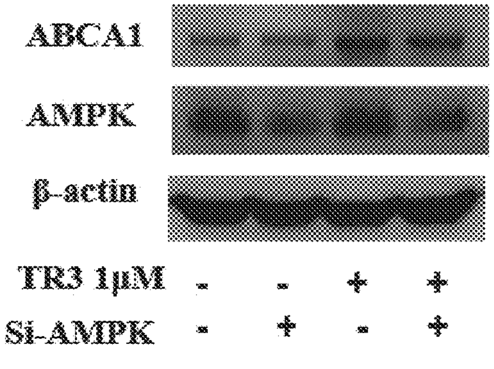
FIG. 11 shows that TR3 significantly up-regulated AMPK levels in cells.

The effect of TR3 on AMPK was detected by western-blot. As shown in FIG. 11, TR3 significantly up-regulated the AMPK level after 18-24 h treatment, indicating it could activate AMPK. The expression of ABCA1 was significantly up-regulated by TR3, which, however, was inhibited by the addition of interfering RNA (si-AMPK).

Finally, it should be noted that the above exploit examples are only used to help the skilled in the art understand the essence of the disclosure and are not used to limit the protection scope of the disclosure.

What is claimed is:

1. An indolo[2',3': 3,4]pyrido[2,1-b]quinazoline compound represented by general formula (I):

(I)

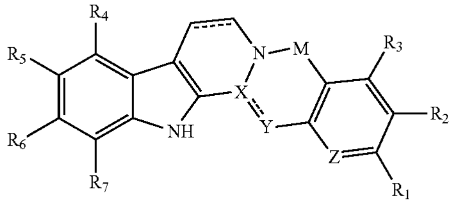

wherein,

M is $C{=}O$;

Z is N;

X is C;

Y is N;

$R_1$ to $R_4$ and $R_6$ are H;

$R_5$ is H; and $R_7$ is methyl or a halogen atom.

2. The compound of claim 1, wherein the compound has a structure as shown in the following table:

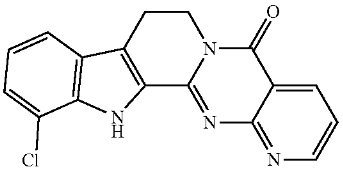

(TR11)

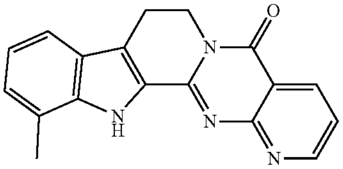

(TR12)

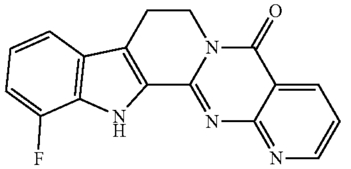

(TR13)

3. A pharmaceutical composition, comprising a therapeutically effective amount of the compound of claim 1, and one or more pharmaceutically acceptable carriers.

4. A pharmaceutical composition, comprising a therapeutically effective amount of the compound of claim 2, and one or more pharmaceutically acceptable carriers.

* * * * *